United States Patent [19]

Chapuis

[11] Patent Number: 5,326,748
[45] Date of Patent: Jul. 5, 1994

[54] CYCLIC ALCOHOLS AND THEIR USE AS PERFUMING INGREDIENTS

[75] Inventor: Christian Chapuis, Mies, Switzerland

[73] Assignee: Firmenich SA, Geneva, Switzerland

[21] Appl. No.: 59,683

[22] Filed: May 10, 1993

[30] Foreign Application Priority Data

Jun. 2, 1992 [CH] Switzerland ............ 1763/92

[51] Int. Cl.$^5$ ............................... A61K 7/46
[52] U.S. Cl. ...................... 512/22; 568/376; 568/377; 568/420; 568/446; 568/826; 568/828
[58] Field of Search ............. 512/22; 568/826, 828, 568/376, 377, 446, 420

[56] References Cited

U.S. PATENT DOCUMENTS

| 2,934,560 | 4/1960 | Kimel | 512/8 |
| 3,492,360 | 1/1970 | Kimel et al. | 512/22 |
| 3,984,354 | 10/1976 | Schleppnik | 512/8 |
| 4,046,716 | 9/1977 | Naegeli | 512/22 |
| 4,278,098 | 7/1981 | Wilson et al. | 131/276 |
| 4,318,831 | 3/1982 | Klein et al. | 512/22 |
| 4,610,813 | 9/1986 | Schulte-Elte et al. | 252/522 |
| 4,696,766 | 9/1987 | Naipawer | 512/8 |

FOREIGN PATENT DOCUMENTS

| 60-109537 | 6/1985 | Japan | 512/8 |
| 516494 | 1/1992 | Switzerland | 512/22 |

OTHER PUBLICATIONS

Chemical Abstracts-Chemical Substance Index, 12th Collective Index, p. 28990CS (1991).
Gergis et al., "Composition of the Essential Oils of *Sideritis cladestina* ssp *cyllenca* and *Sideritis sipylea*", J. Sci. Food Agric. 47 p. 501–507 (1989).

*Primary Examiner*—James H. Reamer
*Attorney, Agent, or Firm*—Pennie & Edmonds

[57] ABSTRACT

The invention relates to compounds of formula

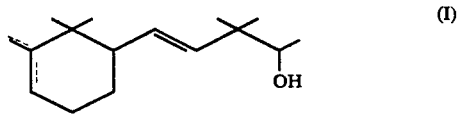

(I)

having a double bond in one of the positions indicated by the dotted lines. Compounds (I) are useful as perfuming ingredients for the preparation of perfuming compositions and perfuming articles, to which they impart sandalwood-animal notes.

11 Claims, No Drawings

CYCLIC ALCOHOLS AND THEIR USE AS PERFUMING INGREDIENTS

BRIEF SUMMARY OF THE INVENTION

The present invention relates to the field of perfumery. It concerns, more particularly, compounds of formula

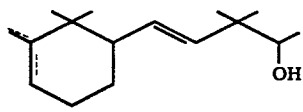

having a double bond in one of the positions indicated by the dotted lines.

The invention also provides a method to confer, improve, enhance or modify the odor of a perfuming composition or a perfumed article, which method comprises adding to said composition or article a fragrance effective amount of a compound of formula (I) as defined above.

Another object of the invention is a perfuming composition or a perfumed article containing as active perfuming ingredient a compound of formula (I) as defined above.

The invention further relates to a process for the preparation of a compound of formula (I) as defined above, which process comprises the reaction of a compound of formula

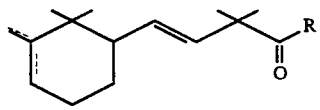

wherein the dotted lines have the meaning indicated in formula (I) and R represents a hydrogen atom or a methyl radical, either with a reducing agent in an inert organic solvent when R is a methyl radical, or with a methyl halomagnesium reagent when R stands for a hydrogen atom.

BACKGROUND OF THE INVENTION

The compounds of formula (I) above are structural homologues of a sandalwood-type fragrant alcohol, i.e. POLYSANTOL ® [3,3-dimethyl-5-(2,2,3-trimethyl-3-cyclopenten-1-yl)-4-penten-2-ol; origin: Firmenich SA, Geneva, Switzerland] which is well appreciated in perfumery. In spite of the abundance of fragrant compounds having a structure similar to that of POLYSANTOL ®, i.e. having an unsaturated cycle with 5 carbon atoms, known to this day (see for example European patent no. 155 591), we found no reference in the literature to any compounds having a homologous structure with 6 carbon atoms.

It is therefore in an expected way that we have now found that compounds (I) according to the invention possess useful odor properties which differ both qualitatively and quantitatively from those of POLYSANTOL ® and other analogue compounds prized by the perfumers.

THE INVENTION

The present invention thus has as one object to provide novel compounds of formula (I) defined above. Compounds (I) possess odor properties which turn out to be extremely useful not only as a result of their basic sandalwood type character, but also, and mostly, as a result of the fact that their sandalwood note is associated with an animal note of the amber type, an odor character that is totally absent from the odor notes of the analogue five-membered ring sandalwood-type compounds. The odor of compounds (I) has the advantage of possessing both the sandalwood and the cedar-amber characters, unlike what is the case with that of the latter analogues, the odor of which is only sandalwood-like.

Amongst the compounds of formula (I), the compound having an endocyclic double bond, or 3,3-dimethyl-5-(2,2,3-trimethyl-3-cyclohexen-1-yl)-4-penten-2-ol, is the one representing at best the desired olfactive characters. It possesses a very strong sandalwood note, very woody, with a natural sandal character and a dry woody note reminiscent of the odor of cedarwood, accompanied by an amber undernote. This compound was preferred by the perfumers in the comparison tests carried out with commercial homologues and which are described further on. As regards the compound (I) having an exocyclic double bond, i.e. 5-(2,2-dimethyl-3-methylene-1-cyclohexyl)-3,3-dimethyl-4-penten-2-ol, it possesses a woody, sandal, sweet note, reminiscent of the odor of the bark and milk of the sandalwood tree. Although its note is less powerful than that of the preceding compound and that of POLYSANTOL ®, it is sweeter and more natural and more reminiscent of the sandalwood essential oil from Mysore origin, which essential oil can be advantageously replaced by compounds (I), as is shown in the examples presented further on.

The compounds of the invention possess two chiral centers and as a result can assume several optically active isomeric forms. While the racemic or optically active mixtures of two or more isomers are advantageous perfuming ingredients, the optically active compounds of formula

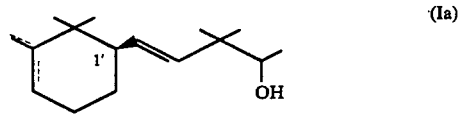

wherein the dotted lines have the meaning indicated in formula (I), as well as their corresponding enantiomers, were also found to be olfactively useful and distinct between themselves.

The compounds according to the present invention can be used in both fine and technical perfumery. They are convenient for the preparation of a variety of perfuming compositions, bases and concentrates, as well as perfumes and colognes, to which they impart very natural sandalwood characters, together with woody-cedar and amber notes. Their use for perfuming varied articles such as soaps, shower or bath gels, shampoos, hairconditioning creams and lotions, cosmetic preparations, body or air deodorants, is also quite advantageous.

Furthermore, they are also quite convenient for perfuming detergents or fabric softeners, as a result of the excellent tenacity of their odor notes, or yet household products.

The proportions in which the compounds according to the invention can be incorporated into the above-mentioned products vary in a wide range of values. The latter depend on the nature of the product one wishes to perfume and on the desired olfactive effect, as well as on the nature of the co-ingredients in a given composition, whenever the compound (I) is used in admixture with current perfuming co-ingredients, solvents or adjuvants. It goes without saying that the compounds according to the invention can also be added to the perfumed compositions and articles alone, or in solution in the usual solvents.

One can cite, for the sake of example, concentrations of the order of 1 to 5%, even 10% or more by weight of compound according to the invention, relative to the weight of the composition into which it is incorporated. Concentrations well below the cited values can be used when the compounds of the invention are employed for perfuming the varied consumer products previously cited.

The invention also relates to a process for the preparation of a compound of formula (I) as defined above, which process comprises the reaction of a compound of formula

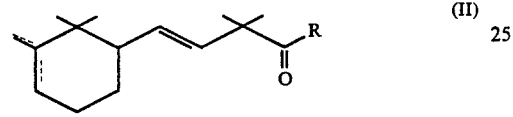
(II)

wherein the dotted lines have the meaning indicated in formula (I) and R represents a hydrogen atom or a methyl radical, either with a reducing agent in an inert organic solvent when R is a methyl radical, or with a methyl halomagnesium reagent when R stands for a hydrogen atom.

According to the first variant of this process, the reaction takes place under classical conditions for the reduction of a ketone into an alcohol and, as reducing agent, one can use any reagent currently used under such conditions.

According to the other variant of the process of the invention, an aldehyde of formula (II) is reacted with a methyl magnesium reagent under the usual conditions of a Grignard-type reaction.

The starting products of formula (II) are novel compounds which can be prepared following the method schematically represented hereinafter.

SCHEME I

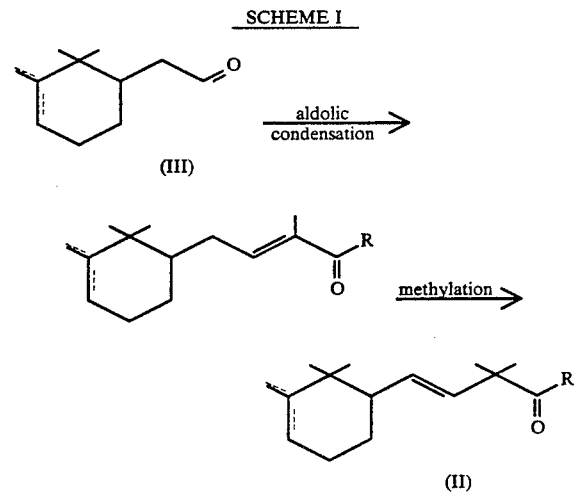

the dotted lines represent a double bond in one of the positions indicated

R=H, CH₃

Aldehydes (III) used as starting products in this scheme are homologues of campholenic aldehyde. Theirs is an original structure and they are prepared as is described in the examples presented further on. The aldolic condensation reactions, which can be condensations of the aldehyde-aldehyde type or of the aldehyde-ketone type depending on the nature of the formula (II) compound one wishes to obtain, are carried out under the usual conditions of this type of reaction, conditions which are described in detail in the examples presented hereinafter. Likewise for the subsequent methylation reactions.

Owing to the chiral center present in the structure of aldehydes (III), the latter can take two enantiomeric forms which, following the reactions represented in scheme I and according to the process of the invention, lead to compounds (II) under two optically active isomeric forms of formula

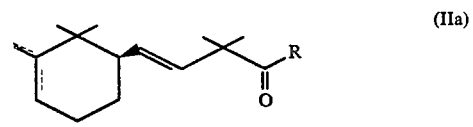
(IIa)

wherein the dotted lines and symbol R have the meaning indicated in formula (II), or to their corresponding enantiomers.

Compounds (IIa), or their corresponding enantiomers, then make it possible to prepare the compounds of formula (Ia) previously mentioned, or respectively their corresponding enantiomers, according to a preferred embodiment of the process of the invention.

The invention will now be described in further detail by way of the following preparation examples, wherein the temperatures are indicated in degrees centigrade and the abbreviations have the usual meaning in the art.

The invention will also be illustrated by way of perfumery application examples presented further on.

EXAMPLE 1

Preparation of (−)-(1′R,E)-3,3-dimethyl-5-(2′,2′,3′-trimethyl-3′-cyclohexen-1′-yl)-4-penten-2-ol a) (−)-(R)-2,2,3-trimethyl-3-cyclohexen-1-acetaldehyde A solution of (−)-(1′R)-2-(2′,2′,3′-trimethyl-3′-cyclopenten-1′-yl)ethyl acetate [prepared as is described by K.-H. Schulte-Elte et al., Helv. Chim. Acta 1989, 72, 1158; $[\alpha]^{20}_D$ (pure)=−1.53°, 395 g, 2.01 mole] in methylene chloride (1000 ml) and methanol (900 ml) was cooled to −40° and an ozone flow passed through the solution (18 g/h) until all the starting product had disappeared. After purging with N₂, dimethylsulfide (DMS, 400 ml) was added dropwise, at −20°. The mixture was kept under stirring overnight at 23° and then concentrated. The raw oil was diluted with cyclohexane (500 ml) and p-toluenesulfonic acid (10 g, 52.6 mmole) was added. The mixture was taken to reflux during 4 h with continuous separation of water. The cooled solution was washed with water, with an aqueous solution saturated with Na₂CO₃, water and brine, then dried over Na₂SO₄ and evaporated. The raw oil (402 g) was distilled in a 12 cm Vigreux column to yield (+)-(1′R)-2-

(6',6'-dimethyl-5'-oxo-3'-cyclohexen-1'-yl)ethyl acetate in the form of a colorless oil (99% pure; yield 65%).

$[\alpha]^{20}_D$ (pure) = +56.2°

P. eb. 85°-89°/7.3 Pa

IR: 2950, 1720, 1660, 1460, 1420, 1380, 1360, 1230 cm$^{-1}$

NMR($^1$H, 360 MHz): 1.00(s, 3H); 1.18(s, 3H); 1.53(m, 1H); 1.93(m, 2H); 2.06(s, 3H); 2.17(m, 1H); 2.52(dt, $J_1$=7 Hz, $J_2$=18 Hz, 1H); 4.12(m, 2H); 5.97(d, J=9 Hz, 1H); 6.84(m, 1H) δ ppm NMR($^{13}$C): 203.8(s); 170.8(s); 146.9(d); 128.2(d); 62.7(t); 45.1(s); 40.5(d); 28.7(t); 28.6(t); 22.3(q); 20.8(q); 18.9(q) δ ppm

MS: 210(1, M+), 150(15), 135(9), 82(73), 68(100), 43(32).

Odor: herbaceous, slightly hay-like, floral, slightly woody.

A solution of this acetate (33.6 g, 0.16 mole) in ethanol (300 ml) was hydrogenated at room temperature and atmospheric pressure during 8 h (5lH$_2$) over Raney Ni (1.4 g). The mixture was filtered, evaporated, dried over Na$_2$SO$_4$ and distilled to provide 32.2 g (yield 95%) of (+)-(1'R)-2-(2',2'-dimethyl-3'-oxo-1'-cyclohexyl)ethyl acetate (97% pure).

$[\alpha]^{20}_D$ (pure) = +64.8°

P. eb. 84°/6.7 Pa

IR: 2950, 1725, 1700, 1360, 1240 cm$^{-1}$

NMR($^1$H, 360 MHz): 1.04(s, 3H); 1.11(s, 3H); 1.45(m, 1H); 1.56(m, 2H); 1.62(m, 1H); 1.86(m, 2H); 2.00(m, 1H); 2.05(s, 3H); 2.31(m, 1H); 2.56(m, 1H); 4.04(m, 1H); 4.17(m, 1H) δ ppm NMR($^{13}$C): 215.3(s); 171.0(s); 63.2(t); 48.7(s); 44.5(d); 37.8(t); 29.1(t); 26.4(t); 25.0(t); 22.7(q); 20.9(q); 19.9(q) δ ppm MS: 212(1, M+), 152(13), 137(41), 124(45), 109(68), 96(42), 81(98), 67(49), 55(57), 43(100).

A solution of this compound (27 g, 0.127 mole) in toluene (500 ml) was added dropwise to a refluxing solution of (tert-butyl) KO (33.6 g, 0.3 mole) and triphenylphosphonium methyl iodide (121.2 g, 0.3 mole). After 3 h, the cooled mixture was poured over ice and extracted with ether (4×100 ml), dried over Na$_2$SO$_4$ and evaporated. The raw oil (29.3 g) was purified by chromatography (SiO$_2$, 580 g, cyclohexane/ethyl acetate 8:2) to yield 19.1 g (yield 72%) of (+)-(1'R)-2-(2',2'-dimethyl-3'-methylene-1'-cyclohexyl)ethyl acetate (98% pure) in the form of a colorless oil.

$[\alpha]^{20}_D$ (pure) = +58.8°

P. eb. 115°/13.3 Pa

IR: 2900, 1705, 1600, 1410, 1330, 1200, 1000, 860 cm$^{-1}$

NMR($^1$H, 360 MHz): 0.95(s, 3H); 1.12(s, 3H); 1.33(m, 4H); 1.72(m, 2H); 1.86(m, 1H); 2.03(s, 3H); 2.20(m, 2H); 4.00(m, 1H); 4.10(m, 1H); 4.65(s, 2H) δ ppm NMR($^{13}$C): 171.1(s); 156.7(s); 105.9(t); 63.9(t); 43.9(d); 39.4(s); 33.1(t); 29.1(t); 27.5(t); 26.6(t); 26.2(q); 22.0(q); 21.0(q) δ ppm MS: 210(0, M+), 150(30), 135(70), 122(67), 107(100), 93(66), 79(86), 67(48), 55(35), 43(53).

A solution of the latter obtained acetate (7 g, 33.3 mmole) and p-toluenesulfonic acid (0.2 g, 1.16 mmole) in toluene (50 ml) was taken to reflux during 2 h. The cooled solution was washed successively with an aqueous solution saturated with NaHCO$_3$ and brine, and dried over Na$_2$SO$_4$. The raw oil was purified by chromatography (SiO$_2$, 520 g, cyclohexane/ethyl acetate 9:1) to yield 4.84 g (yield 70%) of (−)-(1'R)-2-(2',2',3'-trimethyl-3'-cyclohexen-1'-yl)ethyl acetate in the form of a colorless oil.

$[\alpha]^{20}_D$ (pure) = −8.9°

P. eb. 130°/13.3 Pa (bath temp.)

IR: 2900, 1700, 1410, 1325, 1200, 1000 cm$^{-1}$

NMR($^1$H, 360 MHz): 0.89(s, 3H); 1.02(s, 3H); 1.34(m, 3H); 1.64(s, 3H); 1.70(m, 1H); 1.88(m, 1H); 1.95(m, 2H); 2.05(s, 3H); 4.05(m, 1H); 4.19(m, 1H); 5.32(broad s, 1H) δ ppm NMR($^{13}$C): 17.2(s); 140.9(s); 121.6(d); 64.0(t); 41.5(d); 37.1(s); 29.1(t); 26.0(q); 24.9(t); 23.7(t); 21.4(q); 21.0(q); 19.3(q) δ ppm MS: 210(0, M+), 150(23), 135(60), 121(19), 107(100), 96(32), 93(37), 81(53), 69(18), 55(14), 43(27).

A solution of this latter acetate (20 g, 0.095 mole) in ether (80 ml) was added dropwise at −10°, during 40 min, to a suspension of LiAlH$_4$ (2.5 g, 0.066 mole) in ether (400 ml). After 1 h at room temperature, there were added successively, at 0°, water (3 ml), 30% aqueous NaOH (3 ml) and water (9 ml). After 15 min, the mixture was filtered on Celite® and evaporated. The raw oil was distilled in a bulb-to-bulb apparatus (bath temp.: 100°/13.3 Pa) to provide 15.2 g (yield 95%) of (−)-(R)-2-(2',2',3'-trimethyl-3'-cyclohexen-1'-yl)-1-ethanol (99% pure).

$[\alpha]^{20}_D$ (pure) = −12.8°

IR: 3300, 2950, 1440, 1360, 1050 cm$^{-1}$

NMR($^1$H, 360 MHz): 0.89(s, 3H); 1.03(s, 3H); 1.34(m, 4H); 1.50(s, 1H, +D$_2$O, OH); 1.65(d, J=2 Hz, 3H); 1.81(dt, $J_1$=7 Hz, $J_2$=9 Hz, 1 H); 1.95(m, 2H); 3.64(m, 1H); 1.75(m, 1H); 5.32(broad s, 1H) δ ppm NMR($^{13}$C): 141.1(s); 121.6(d); 62.2(t); 41.2(d); 37.1(s); 33.3(t); 26.0(q); 25.1(t); 23.9(t); 21.4(q); 19.3(q) δ ppm MS: 168(17, M+), 150(9), 135(37), 123(62), 107(72), 96(53), 93(40), 81(100), 69(40), 55(29), 41(43).

A solution of the above-prepared alcohol (16.6 g, 0.988 mole) in 20 ml of CH$_2$Cl$_2$ was added dropwise to a suspension of pyridinium chlorochromate (PCC, 35 g, 0.162 mole) and Celite® (50 g) in CH$_2$Cl$_2$ (450 ml). The mixture was kept under stirring during 1 h at room temperature, filtered on Celite®, then on SiO$_2$ with ether, evaporated and distilled on a bulb-to-bulb apparatus (bath temp.: 100°/13.3 Pa) to yield 15.1 g (yield 92%) of the desired (−)-(R)-2,2,3-trimethyl-3-cyclohexene-1-acetaldehyde (98% pure).

$[\alpha]^{20}_D$ (pure) = −37.5°

IR: 2960, 2720, 1720, 1440, 1360 cm$^{-1}$

NMR($^1$H, 360 MHz): 0.90(s, 3H); 1.06(s, 3H); 1.43(m, 1H); 1.60(m 1H); 1.66(d, J=2Hz, 3H); 1.98(m, 2H); 2.03(dt, $J_1$=2 Hz, $J_2$=8 Hz, 1H); 2.21(ddd, $J_1$=2, $J_2$=8, $J_3$=15 Hz, 1H); 2.58(dd, $J_1$=2, $J_2$=15 Hz, 1H); 5.35(broad s, 1H); 9.79(dd, $J_1$=1, $J_2$=3 Hz, 1H) δ ppm NMR($^{13}$C): 203.2(d); 140.3(s); 121.7(d); 45.4(t); 39.2(d); 36.8(s); 26.4(q); 24.7(t); 24.4(t); 22.0(q); 19.3(q) δ ppm MS: 166(11, M+), 133(25), 121(39), 107(100), 96(26), 91(31), 81(62), 69(20), 55(18), 41(32).

Odor: aldehydic, green, lemon; head-note: fat, camphor.

b) (−)-(1'R,E)-4-(2',2',3'-trimethyl-3'-cyclohexen-1'-yl)-2-methyl-2-butenal

In a flask under N$_2$, 0.470 ml of 40% NaOH were placed in 15.66 ml of methanol. The mixture was heated to reflux and a mixture of 13 g (78.3 mmole) of the aldehyde obtained according to a) and 156.6 mmole of propanal was introduced over 1 h, while maintaining the reflux until completion of the reaction. The disappearance of the starting product was controlled by gas phase chromatography. After letting the reaction mixture cool down, 15.66 ml of water and ice were added. The aqueous phase was decanted, taken in petroleum ether 30/50 and neutralized with water. The mixture was dried, concentrated, purified by SiO₂ chromatography with cyclohexane/ethyl acetate 95:5 and distilled in a bulb-to-bulb apparatus (bath temp.: 120°/26.6 Pa) to yield 7.7 g (yield 47%) of the desired butenal (95% pure).

[α]²⁰$_D$ (pure) = −36.9°

IR: 2970, 1690, 1640, 1450, 1360, 1210, 1060, 800 cm⁻¹

NMR(¹H, 360 MHz): 0.97(s, 3H); 1.1(s, 3H); 1.4(m, 1H); 1.53(m, 1H); 1.61(m, 1H); 1.66(d, J=2 Hz, 3H); 1.77(s, 3H); 1.95(m, 2H); 2.18(m, 1H); 2.5(m, 1H); 5.35(broad s, 1H); 6.55(broad t, J=7 Hz, 1H); 9.43(s, 1H) δ ppm NMR(¹³C): 9.36(q); 19.3(q); 21.7(q); 23.9(t); 24.8(t); 26.4(q); 29.9(t); 37.3(s); 45.0(d); 121.7(d); 140.1(s); 140.5(s); 155.2(d); 195.0(d) δ ppm

MS: 206(16, M+), 173(15), 163(17), 136(50), 121(51), 107(62), 81(100), 41(41).

Odor: fatty, aldehydic.

c) (−)-(1'R,E)-4-(2',2',3'-trimethyl-3'-cyclohexen-1'-yl)-3-penten-2-one

In a vessel under N₂, 17.8 mmole of NaOH were dissolved in 1.056 mole of methanol. The mixture was cooled to −5° and 0.198 mole of ethyl-methyl-ketone added thereto. 5.5 G (33 mmole) of the aldehyde obtained according to a) were introduced. The mixture was stirred during 24 h at −5° and then 24 h at room temperature. There were added 1.254 g of 60% H₂SO₄. After having concentrated the methanol, the product was taken in 30/50 petroleum ether and neutralized. After drying, concentration and SiO₂ chromatography with cyclohexane/ethyl acetate 9:1, there were obtained 6.5 g (yield 89%) of the desired pentenone (99% pure).

[α]²⁰$_D$ (pure) = −33,12°

IR: 2970, 1690, 1590, 1440, 1360, 1280, 1080 cm⁻¹

NMR(¹H, 360 MHz): 0.96(s); 1,10(s); 1,3–1,65(m, 4H); 1,67(s, 3H); 1,79(s, 3H); 1,95(m, 2H); 2,07(m, 1H); 2,33(s, 3H); 2,41(m, 1H); 5,35(broad s, 1H); 6,68(broad t, J=7 Hz, 1H) δ ppm NMR(¹³C): 11,4(q); 19,3(q); 21,7(q); 23,9(t); 24,9(t); 25,5(q); 26,4(q); 30,0(t); 37,3(s); 45,1(d); 121,7(d); 138,3(s); 140,6(s); 144,2(d); 199,7(s) δ ppm MS: 220(8, M+), 205(5), 187(8), 177(15), 150(28), 135(23), 121(60), 107(58), 81(100), 43(85).

Odor: slightly sandalwood, vegetable, cabbage.

d) (−)-(1'R)-3,3-dimethyl-5-(2',2',3'-trimethyl-3'-cyclohexen-1'-yl)-4-penten-2-one In a dried flask, under N₂, 20.4 mmole of potassium tert-butylate were dissolved in 11.9 ml of DMSO. The temperature was brought to around 20° and 3.8 g (17 mmole) of the ketone prepared according to c) were introduced. The mixture was allowed to react for 30 min. After cooling to about 5°, 20.4 mmole of CH₃I were added. The temperature was allowed to increase and the mixture was taken in 30/50 petroleum ether and washed to neutrality with water. 2.8 G of the desired pentenone were obtained (yield 70%).

[α]²⁰$_D$ (pure) = −24.12°

IR: 2970, 1710, 1470, 1360, 1120, 980 cm⁻¹

NMR(¹H, 360 MHz): 0.89(s, 3H); 0.99(s, 3H); 1.23(s, 6H); 1.58(m, 2H); 1.66(d, J=2 Hz, 3H); 2.0(m, 3H); 2.12(s, 3H); 5.34(broad s, 1H); 5.55(m, 2H) δ ppm NMR(¹³C): 19.2(q); 22.5(q); 24.2(q); 24.6(t); 25.4(t); 26.7(q); 37.1(s); 49.2(d); 50.3(s); 121.5(d); 132.5(d); 135.0(d); 140.7(s); 211.4(s) δ ppm MS: 234(1, M+), 191(22), 135(22), 121(65), 95(100), 81(78), 69(98), 55(29), 43(47).

Odor: woody, fruity.

e) (−)-(1'R,E)-2,2-dimethyl-4-(2',2',3'-trimethyl-3'-cyclohexen-1'-yl)-3-butenal Following a method analogous to that described under d), 2 g (9.7 mmole) of the aldehyde prepared according to b) were methylated. After chromatography on a SiO₂ column, with 3:97 ethyl acetate/cyclohexane, 1.8 g (yield 84%) of the desired butenal were obtained.

P. eb. 120°/40 Pa (bath temp.)

[α]²⁰$_D$ (pure) = −22.15°

IR: 2970, 1730, 1465, 1360, 980 cm⁻¹

NMR(¹H, 360 MHz): 9.35(s, 1H); 5.55(dd, J₁=8, J₂=13 Hz, 1H); 5.38(d, J=13 Hz, 1H); 5.32(broad s, 1H); 2.0(m, 3H); 1.67(s, 3H); 1.58(m, 2H); 1.19(s, 6H); 0.98(s, 3H); 0.85(s, 3H) δ ppm

MS: 220(1, M+), 121(11), 96(100), 81(50), 69(17), 55(12), 41(23).

f) In a flask under N₂, 8 mmole of LiAlH₄ were dissolved in 12 ml of tetrahydrofuran (THF). 1.87 G (8 mmole) of the pentenone prepared according to d), diluted in 50 ml of THF, were introduced dropwise, while maintaining the temperature between 20° and 30°. Reaction was allowed during 1 h. After concentrating the THF, the mixture was taken in petroleum ether 30/50, washed to neutrality with 15% HCl, dried, concentrated and distilled to provide 1.8 g (yield 95%) of (−)-(1'R,E)-3,3-dimethyl-5-(2',2',3'-trimethyl-3'-cyclohexen-1'-yl)-4-penten-2-ol (97% pure).

The same compound was obtained by reacting the aldehyde obtained according to e) with a methyl-magnesium reagent, for example CH₃MgI.

[α]²⁰$_D$ (pure) = −20.08°

IR: 3400, 2970, 1465, 1360, 1095, 980, 910 cm⁻¹

NMR(¹H, 360 MHz): 0.89(s, 3H); 1.0(s, 9H); 1.11(d, J=7 Hz, 3H); 1.58(m, 2H); 1.66(broad s, 3H); 2.0(m, 3H); 3.5(m, 1H); 5.33(broad s, 1H); 5.46(m, 2H) δ ppm NMR(¹³C): 17.5(q); 19.3(q); 22.3(q); 22.5(q); 23.9(q); 24.7(t); 25.7(t); 26.7(q); 36.9(s); 40.9(s); 49.3(d); 74.4(d); 121.5(d); 131.5(d); 137.4(s); 140.9(s) δ ppm

MS: 236(0, M+), 192(11), 135(10), 121(45), 96(100), 81(78), 69(44), 41(28).

Odor: described above.

EXAMPLE 2

Preparation of (+)-(1'R,E)-5-(2',2'-dimethyl-3'-methylene-1'-cyclohexyl)-3,3-dimethyl-4-penten-2-ol a) (+)-(R)-2,2-dimethyl-3-methylene-1-cyclohexaneacetaldehyde To a suspension of LiAlH₄ (0.4 g, 10.5 mmole) in ether (50 ml) there was added dropwise at −10° a solution of (+)-(1'R)-2-(2',2'-dimethyl-3'-methylene-1'-cyclohexyl)ethyl acetate [see Example 1a; 3.6 g, 17.1 mmole] in ether (20 ml). After 1 h at room temperature, there were added successively, at 0°, water (0.4 ml), 15% aqueous NaOH (0.4 ml) and water (1.2 ml). The mixture was filtered on Celite ® and evaporated. The raw oil (2.9 g) was distilled in a bulb-to-bulb apparatus (bath temp.: 100°/13.3 Pa) to provide 2.77 g (yield 97%) of (+)-(1'R)-2-(2',2'-dimethyl-3'-methylene-1'-cyclohexyl)-1-ethanol in the form of a colorless oil.

$[\alpha]^{20}_D$(pure) = +69°

IR: 3300, 2920, 1630, 1440, 1380, 1160, 1050, 890 cm$^{-1}$

NMR($^1$H, 360 MHz): 0.96(s, 3H); 1.13(s, 3H); 1.3(m, 4H); 1.45(broad s, 1H,+D$_2$O—OH); 1.74(m, 2H); 1.79(m, 1H); 2.2(m, 2H); 3.59(m, 1H); 3.69(m, 1H); 4.65(s, 2H) δ ppm NMR($^{13}$C): 157.0(s); 105.7(t); 62.2(t); 43.7(d); 39.4(s); 33.4(t); 33.2(t); 27.7(t); 26.8(t); 26.2(q); 22.0(q) δ ppm MS: 168(8, M+), 153(11), 135(41), 123(61), 107(100), 93(45), 79(99), 67(94), 55(70), 41(68).

Odor: vaguely camphor, green, chemical.

To a suspension of pyridinium chlorochromate (PCC, 30 g, 0.139 mole) and 45 g of Celite ® in CH$_2$Cl$_2$ (300 ml) there was added dropwise, over 1 h, a solution of the alcohol obtained here-above (15.5 g, 0.092 mole) in CH$_2$Cl$_2$ (100 ml). The mixture was maintained under stirring for 1 h at room temperature. It was filtered on SiO$_2$ (150 g), washed with ether and evaporated to provide 16.3 g of raw oil. The latter was distilled in a bulb-to-bulb apparatus (bath temp.: 100°/13.3 Pa) to yield 15.2 g (yield 99%) of the desired acetaldehyde, 97% pure.

$[\alpha]^{20}_D$(pure) = +20.5°

IR: 2940, 1720, 1630, 890 cm$^{-1}$

NMR($^1$H, 360 MHz): 0.96(s, 3H); 1.14(s, 3H); 1.40(m, 2H); 1.70(m, 2H); 1.94(m, 1H); 2.15(m, 1H); 2.22(m, 2H); 2.57(m, 1H); 4.70(d, J=7 Hz, 2H); 9.74(t, J=2 Hz, 1H) δ ppm NMR($^{13}$C): 202.7(d); 155.6(s); 106.6(t); 45.6(t); 41.3(d); 39.1(s); 32.9(t); 28.6(t); 26.4(q); 26.2(t); 22.5(q) δ ppm MS: 166(4, M+), 151(10), 133(45), 122(61), 107(100), 91(35), 79(58), 67(50), 55(40), 41(49).

Odor: green, aldehydic, minty.

b) (+)-(1'R,E)-5-(2',2'-dimethyl-3'-methylene-1'-cyclohexyl)-3-methyl-3-penten-2-one A method analogous to that described in example 1c) was followed using 22.68 mmole of NaOH in 1.344 mole of methanol, 0.252 mole of ethyl-methyl-ketone, 7 g (42 mmole) of the aldehyde prepared according to a) above and 1.596 g of H$_2$SO$_4$. After chromatography on SiO$_2$ with toluene/ethyl acetate 97:3, there were obtained 3.99 g (yield 43%) of the desired pentenone (97% pure).

$[\alpha]^{20}_D$(pure) = +32.35°

IR: 2930, 1670, 1640, 1440, 1360, 1280, 1160, 1080, 890 cm$^{-1}$

NMR($^1$H, 360 MHz): 1.03(s, 3H); 1.99(s, 3H); 1.35(m, 3H); 1.75(m, 2H); 1.78(s, 3H); 2.05(dt, J$_1$=9, J$_2$=15 Hz, 1H); 2.21(m, 2H); 2.3(s, 3H); 2.4(m, 1H); 4.68(s, 2H); 6.63(t, J=7 Hz, 1H) δ ppm NMR($^{13}$C): 11.3(q); 22.2(q); 25.4(q); 26.5(q); 26.6(t); 27.7(t); 30.0(t); 33.0(t); 39.6(s); 47.4(d); 106.1(t); 138.0(s); 144.0(d); 156.3(s); 199.6(s) δ ppm MS: 220(4, M+), 205(5), 148(29), 133(31), 123(50), 107(26), 98(36), 93(30), 81(100), 67(50).

Odor: sandalwood, milky. c) (+)-(1'R,E)-5-(2',2'-dimethyl-3'-methylene-1'-cyclohexyl)-3,3-dimethyl-4-penten-2-one Following a method analogous to that described in example 1d), 3.9 g (17.7 mmole) of the ketone prepared according to b) above were methylated by means of 21.24 mmole of (tert-butyl)KO in 12.4 ml of DMSO, and 21.24 mmole of CH$_3$I. After chromatography on SiO$_2$ with cyclohexane/ethyl acetate 95:5, 3.42 g (yield 83%) of the desired pentenone (98.7% pure) were obtained.

P. eb. 100°/13.3 Pa (bath temp.)

$[\alpha]^{20}_D$(pure) = +55.32°

IR: 2960, 2930, 1710, 1640, 1470, 1360, 1120, 980, 890 cm$^{-1}$

NMR($^1$H, 360 MHz): 0.95(s, 3H); 1.06(s, 3H); 1.21(s, 3H); 1.22(s, 3H); 130-1.95 (m, 5H); 2.1(s, 3H); 2.2(m, 2H); 4.64(s, 1H); 4.65(s, 1H); 5.5(m, 2H) δ ppm NMR($^{13}$C): 22.5(q); 24.2(q); 25.4(q); 26.7(t); 26.8(q); 29.1(t); 33.0(t); 39.3(s); 50.3(s); 51.7(d); 105.9(t); 132.1(d); 135.2(d); 156.3(s); 211.3(s) δ ppm MS: 234(1, M+), 191(14), 148(9), 135(19), 121(21), 109(23), 95(27), 69(100), 43(23).

d) A method analogous to that described in example 1f) was followed, using 11 mmole of LiAlH$_4$ in 16.5 ml of THF and 2.6 g (11 mmole) of the ketone prepared according to c) above. After chromatography on SiO$_2$ with toluene/ethyl acetate 9:1, there were obtained 1.83 g (yield 70%) of (+)-(1'R,E)-5-(2',2'-dimethyl-3'-methylene-1'-cyclohexyl)-3,3-dimethyl-4-penten-2ol (97% pure).

P. eb. 80°/6.7 Pa (bath temp.) $[\alpha]^{20}_D$(pure) = +55.74°

IR: 3400, 2970, 2950, 1640, 1450, 1380, 1070 cm$^{-1}$

NMR($^1$H, 360MHz): 0.96(s, 3H); 0.99(s, 6H); 1.07(s, 3H); 1.11(d, J=7 Hz, 3H); 1.3-1.9(m, 5H); 2.2(m, 2H); 3.48(m, 1H); 4.65(d, J=3 Hz, 2H); 5.4(m, 2H) δ ppm NMR($^{13}$C): 17.6(q); 22.5(2x q); 23.8(q); 26.8(t); 26.9(q); 29.5(t); 33.0(t); 39.1(s); 40.9(s); 51.8(d); 74.4(d); 105.7(t); 130.9(d); 137.6(d); 156.6(s) δ ppm MS: 236(0, M+), 218(1), 192(18), 149(19), 135(21), 121(25), 109(28), 93(46), 69(100), 55(27).

Odor: described above

EXAMPLE 3

Preparation of (+)-(1'S, E)-3,3-dimethyl-5-(2',2',3'-trimethyl-3'-cyclohexen-1'-yl)-4-penten-2-ol This compound was prepared in an analogous way to that described in example 1, but starting from the enantiomer of the acetate used as starting product in example 1 a). This acetate was prepared in an analogous way to that described by K. H. Schulte-Elte et al., Helv. Chim. Acta 1989, 1158, starting from the appropriate isomer of campholenic aldehyde having $[\alpha]^{20}_D$(pure) = −9.6°.

The analytical data of the obtained compounds were identical to those of their corresponding enantiomers described in example 1, with the exception of the optical rotation angles presented hereinafter.

(+)-(1'S)-2-(2',2',3'-trimethyl-3'-cyclopenten-1'-yl)ethyl acetate $[\alpha]^{20}_D$(pure) = +1.2°

(−)-(1'S)-2-(6',6'-dimethyl-5'-oxo-3'-cyclohexen-1'-yl)ethyl acetate $[\alpha]^{20}_D$(pure) = −62.5°

(−)-(1'S)-2-(2',2'-dimethyl-3'-oxo-1'-cyclohexyl)ethyl acetate $[\alpha]^{20}_D$(pure) = −71.2°

This acetate was transformed into the corresponding isomer of 2-(2',2'-dimethyl-3'-methylene-1'-cyclohexyl)ethyl acetate according to the process described in example 1a), which isomer, without having been isolated, was transformed according to example 2a), 1st paragraph, into the corresponding alcohol presented hereinafter: (−)-(S)-2-(2',2'-dimethyl-3'-methylene-1'-cyclohexyl)-1-ethanol $[\alpha]^{20}_D$(pure) = −74.4°

This alcohol was then transformed into its bonding isomer in an analogous way to that described in example 1a) for the corresponding acetates.

(+)-(S)-2-(2',2',3'-trimethyl-3'-cyclohexen-1'-yl)-1-ethanol
[α]$^{20}_D$(pure) = +12.7°

(+)-(S)-2,2,3-trimethyl-3-cyclohexene-1-acetaldehyde
[α]$^{20}_D$(pure) = +38.3°

(+)-(1'S,E)-3-methyl-5-(2',2',3'-trimethyl-3'-cyclohexene-1'-yl)-3-penten-2-one
[α]$^{20}_D$(pure) = +29.6°

(+)-(1'S,E)-3,3-dimethyl-5-(2',2',3'-trimethyl-3'-cyclohexen-1'-yl)-4-penten-2-one
[α]$^{20}_D$(pure) = +24.9°

(+)-(1'S,E)-3,3-dimethyl-5-(2',2',3'-trimethyl-3'-cyclohexene-1'-yl)-4-penten-2-ol
[α]$^{20}_D$(pure) = +20.7°

EXAMPLE 4

Preparation of (−)-(1'S,E)-5-(2',2'-dimethyl-3'-methylene-1'-cyclohexyl)-3,3-dimethyl-4-penten-2-ol This compound was prepared in an analogous way to that described in example 2, starting from (−)-(S)-2-(2',2'-dimethyl-3'-methylene-1'-cyclohexyl)-1-ethanol ([α]$_D^{20}$(pure) = −74.4°; described in example 3). The analytical data of the obtained compounds were identical to those of their corresponding enantiomers described in example 2, with the exception of the optical rotation angles presented hereinafter.

(−)-(S)-2,2-dimethyl-3-methylene-1-cyclohexaneacetaldehyde
[α]$_D^{20}$(pure) = 21.6°

(−)-(1'S,E)-5-(2',2'-dimethyl-3'-methylene-1'-cyclohexyl)-3-methyl-3-penten-2-one
[α]$_D^{20}$(pure) = −38.0°

(−)-(1'S,E)-5-(2',2'-dimethyl-3'-methylene-1'-cyclohexyl)-3,3-dimethyl-4-penten-2-one [α]$_D^{20}$(pure) = −52.6°

(−)-(1'S,E)-5-(2',2'-dimethyl-3'-methylene-1'-cyclohexyl)-3,3-dimethyl-4-penten-2-ol [α]$_D^{20}$(pure) = −64.6°

Odor: sandalwood.

EXAMPLE 5

Perfuming of a Soap

100 G of a soap in chips obtained from a non-perfumed sodium soap base prepared from coconut oil and tallow, were admixed with 0.5 g de (−)-(1'R,E)-3,3-dimethyl-5-(2',2',3'-trimethyl-3'-cyclohexen-1'-yl)-4-penten-2-ol on the one hand, and of (+)-(1'R,E)-5-(2',2'-dimethyl-3'-methylene-1'-cyclohexyl)-3,3-dimethyl-4-penten-2-ol on the other hand, until obtaining homogeneous pastes. The soap compositions thus obtained possessed, in the first case, an odor which was both sandalwood and amber-like, and in the second case, a woody odor of the natural sandalwood type.

EXAMPLE 6

Perfuming Composition

A base perfuming composition was prepared by admixing the following ingredients:

| Ingredients | Parts by weight |
| --- | --- |
| 10%* Decanal | 10 |
| 10%* Undecylenic aldehyde | 40 |
| 10%* Dodecanal | 10 |
| 10%* Methylnonylacetic aldehyde | 10 |
| Artemisia essential oil | 10 |
| 10%* Castoreum oil | 20 |
| 10%* Civet oil | 10 |
| Galbanum resinoid essential oil | 10 |
| 50%* Jasmin absol. | 100 |
| Olibanum oil | 10 |
| Patchouli oil | 30 |
| Styrallyl acetate | 15 |
| α-Isomethylionone | 95 |
| Coriander oil | 5 |
| Levocitronellol | 50 |
| 10%* Exaltolide ®[1)] | 50 |
| Synth. jasmin oil | 100 |
| Synth. bergamote | 100 |
| Sicily lemon oil | 40 |
| 50%* Oakmoss absol. | 30 |
| Synth. neroli | 20 |
| Galaxolide ® 50[2)] | 50 |
| Coumarine | 50 |
| Tonalide ®[3)] | 40 |
| Dihydromyrcenol[4)] | 75 |
| Total | 980 |

*in dipropyleneglycol (DIPG)
[1)]cyclopentadecanolide; origin: Firmenich SA, Geneva, Switzerland
[2)]1,3,4,6,7,8-hexahydro-4,6,6,7,8,8-hexamethyl-cyclopenta[g]isochromene; origin: International Flavors & Fragrances Inc., USA
[3)]7-acetyl-1,1,3,4,4,6-hexamethyltetraline; origin: PFW, Holland
[4)]2,6-dimethyl-7-octen-2-ol; origin: International Flavors & Fragrances Inc., USA.

Upon adding to 98 g of this base composition of the woody-animal type 2 g of (+)-(1'R,E)-5-(2',2'-dimethyl-3'-methylene-1'-cyclohexyl)-3,3-dimethyl-4-penten-2-ol, there was obtained a novel composition which developed an odor the sandalwood character of which was clearly perceptible. On the other hand, when the above-mentioned compound according to the invention was replaced by (−)-(1'R,E)-3,3-dimethyl-5-(2',2',3'-trimethyl-3'-cyclohexen-1'-yl)-4-penten-2-ol, there was obtained a novel composition the odor of which had a weaker sandalwood-like caracter but distinctly more amber-like than that of the preceding novel composition.

In both cases it was found that the compounds according to the invention replaced with advantage the natural sandalwood essential oil (origin: Mysore) of which a double amount would have been necessary to produce a similar effect. The use of these compounds is therefore all the more advantageous since the natural sandalwood essential oil is very expensive and rare.

EXAMPLE 7

Perfuming Composition

A base perfuming composition was prepared by admixing the following ingredients:

| Ingredients | Parts by weight |
| --- | --- |
| p-tert-Butylcyclohexyl acetate | 150 |
| Cedroxyde ®[1)] | 100 |
| Florida orange oil | 100 |
| Dihydroterpenyl acetate | 70 |
| α-Methylionone | 60 |
| Bourbon geranium oil | 50 |
| Lavender oil | 40 |
| Vertofix coeur[2)] | 40 |
| Mayol ®[3)] | 40 |
| Florol ®[4)] | 40 |
| Musc ketone | 30 |
| Isoeugenol | 30 |
| 10%* Ambrox ® DL[5)] | 30 |
| Myrcenyl acetate[6)] | 30 |
| Rosinol | 20 |
| Amyl salicylate | 20 |

| Ingredients | Parts by weight |
| --- | --- |
| TCD acetate[7] | 20 |
| Synth. bergamote | 10 |
| Cyclohexylethanol acetate | 20 |
| 10%* Cristal moss | 20 |
| Synth. neroli | 10 |
| 1%* β-Damascenone | 10 |
| Dihydromyrcenol[8] | 10 |
| Total | 950 |

*in DIPG
[1] trimethyl cyclododecatriene epoxyde; origin: Firmenich SA, Geneva, Switzerland
[2] origin: International Flavors & Fragrances, Inc., USA
[3] hydroxymethyl isopropyl cyclohexane; origin: Firmenich SA, Geneva, Switzerland
[4] tetrahydro-2-isobutyl-4-methyl-4(2H)-pyranol; origin: Firmenich SA, Geneva, Switzerland
[5] tetramethyl perhydronaphthofuran; origin: Firmenich SA, Geneva, Switzerland
[6] 2-methyl-6-methylene-7-octen-2-yl acetate; origin: International Flavors & Fragrances, Inc., USA
[7] (tricyclo[5.2.1.0$^{2,6}$]dec-4-yl)methyl acetate; origin: Firmenich SA, Geneva, Switzerland
[8] see example 6

With this base composition of the floral-woody type four compositions were prepared, according to the following table:

| Ingredients | Composition/Weight in g | | | |
| --- | --- | --- | --- | --- |
| | A | B | C | D |
| Base | 95 | 95 | 95 | 95 |
| (−)-(1'R,E)-3,3-dimethyl-5-(2',2',3'-trimethyl-3'-cyclohexen-1'-yl)-4-penten-2-ol | 5 | — | — | — |
| (+)-(1'R,E)-5-(2',2'-dimethyl-3'-methylene-1'-cyclohexyl)-3,3-dimethyl-4-penten-2-ol | — | 5 | — | — |
| POLYSANTOL ® | — | — | 5 | — |
| BACDANOL ®[1] | — | — | — | 5 |

[1] 2-ethyl-4-(2,2,3-trimethyl-3-cyclopenten-1-yl)-2-buten-1-ol, from IFF Inc.

These four compositions A to D were evaluated on a blind test by a panel of 8 expert perfumers. The latter unanimously preferred composition A for the superiority of its olfactive note, both from the point of view of its character and from that of its strength. On the other hand, composition C was generally preferred to composition B, which was nevertheless judged olfactively more interesting and pleasant than composition D.

What I claim is:

1. Compound of formula

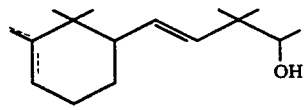

(I)

having a double bond in one of the positions indicated by the dotted lines.

2. Compound according to claim 1, in the form of an optically active isomer of formula

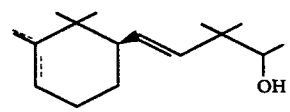

(Ia)

wherein the dotted lines have the meaning indicated in formula (I), or of its corresponding enantiomer.

3. (−)-(1'R,E)-3,3-Dimethyl-5-(2',2', 3',-trimethyl-3'-cyclohexen-1'-yl)4-penten-2-ol.

4. Method to confer, improve, enhance or modify the odor properties of a perfuming composition or a perfumed article, which method comprises adding to said composition or article a fragrance effective amount of a compound according to any one of claims 1 to 3.

5. Perfuming composition containing as an active perfuming ingredient a compound according to any one of claims 1 to 3.

6. Perfumed article containing as an active perfuming ingredient a compound according to any one of claims 1 to 3.

7. Perfumed article according to claim 6, in the form of a perfume or a cologne, a soap, a shower or bath gel, a shampoo or a hair-conditioner, a cosmetic preparation, a body or air deodorant, a detergent, a fabric softener or a household product.

8. Compound of formula

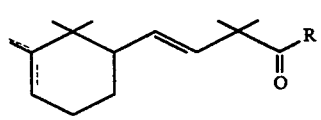

(II)

having a double bond in one of the positions indicated by the dotted lines and wherein symbol R represents a hydrogen atom or a methyl radical.

9. Compound according to claim 8, in the form of an optically active isomer of formula

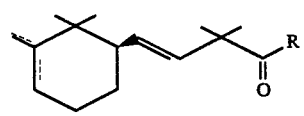

(IIa)

wherein the dotted lines and symbol R have the meaning indicated in formula (II), or of its corresponding enantiomer.

10. Compound of formula

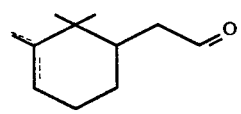

(III)

having a double bond in one of the positions indicated by the dotted lines.

11. Compound according to claim 10, in the form of an optically active isomer of formula

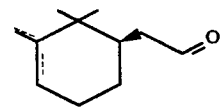

(IIIa)

wherein the dotted lines have the meaning indicated in formula (III), or of its corresponding enantiomer.

* * * * *